United States Patent [19]

Prusoff et al.

[11] 4,000,260
[45] Dec. 28, 1976

[54] ANTI HERPES SIMPLEX VIRAL COMPOUNDS AND THEIR SYNTHESIS

[75] Inventors: H. William Prusoff, Branford, Conn.;
Yung-Chi Cheng, Amherst, N.Y.;
David C. Ward, Guilford, Conn.;
John P. Neenan, Detroit, Mich.

[73] Assignee: Research Corporation, New York, N.Y.

[22] Filed: Aug. 15, 1975

[21] Appl. No.: 604,481

Related U.S. Application Data

[63] Continuation-in-part of Ser. No. 501,767, Aug. 29, 1974, abandoned.

[52] U.S. Cl. .................................. 424/180; 536/23

[51] Int. Cl.$^2$ .......................................... A61K 31/70
[58] Field of Search .............. 424/180; 260/211.5 R

*Primary Examiner*—Jerome D. Goldberg
*Attorney, Agent, or Firm*—Cooper, Dunham, Clark, Griffin & Moran

[57] ABSTRACT

The compounds 5'-amino-2',5'-dideoxy-5-iodouridine; 5'-amino-2',5'-dideoxy-5-bromouridine; and the pharmaceutically acceptable acid addition salts thereof have been found to be potent inhibitors of herpes simplex virus.

7 Claims, No Drawings

ANTI HERPES SIMPLEX VIRAL COMPOUNDS AND THEIR SYNTHESIS

The invention described herein was made in the course of work under a grant or award from the Department of Health, Education and Welfare.

RELATED APPLICATION

This application is a continuation-in-part of copending application Ser. No. 501,767, now abandoned which was filed on Aug. 29, 1974.

BACKGROUND OF THE INVENTION

Herpes simplex viruses are the causative agents in a number of mammalian infections, for example, such human diseases a keratitis, herpes labialis (cold sores), cutaneous herpes, herpes zoster, herpes genitalis, herpes encephalitis, neonatal herpes, herpetic whitlow and acute herpetic gingivostomatitis. Poxviruses, especially poxuirus variolae, are the causative agents of smallpox in man. No completely satisfactory antiviral agent combining high potency and low toxicity has yet been discovered. Accordingly, considerable research effort has been expended in attempts to discover a suitable agent.

THE INVENTION

It has now been discovered that compounds selected from the group consisting of 5'-amino-2',5'-dideoxy-5-iodouridine; 5'-amino-2',5'-dideoxy-5-bromouridine and their pharmaceutically acceptable acid addition salts are potent inhibitors of herpes simplex virus, and are substantially non-toxic. For convenience, these compounds will hereinafter be referred to as AIU and ABrU. This invention relates to these novel compounds and to therapeutically useful compositions containing one or more of them, whether or not associated with other therapeutically active ingredients.

The following example illustrates the synthesis of AIU and ABrU. Pharmaceutically acceptable acid addition salts are readily prepared by treatment of the basic compound with acid in aqueous media followed by evaporation of the solvent, for example, by freeze drying. The salts are generally more soluble than the free base, and are often preferred for the preparation of water based dosage forms such as eye drops. For example, a suspension of free amine in distilled water may be treated with an equivalent amount of aqueous acid, and the resulting solution stabilized with a buffer, such as phosphate buffered saline.

The acids which may be used to prepare the pharmaceutically acceptable acid addition salts of this invention are those containing non-toxic anions and include, for example, hydrochloric, sulfuric, phosphoric, acetic, lactic, citric, tartaric, oxalic, succinic, maleic, gluconic, saccharic and the like.

EXAMPLE I

Synthesis of 5'-amino-2',5'-dideoxy-5-iodouridine 1. 5'-O-Tosyl-2'-deoxyuridine 22.8 gm of deoxyuridine (100 mmoles) are dissolved in 100 ml of freshly distilled, dry pyridine and kept on ice at 4° C. Freshly recrystallized p-toluenesulfonyl chloride (22 gm, 115 mmoles) is dissolved in a separate 100 ml of cold pyridine an then slowly added to the nucleoside solution. The reaction mixture is left standing at 4° C for 24 hours and the solution poured into 400 ml of ice water. This solution is then extracted twice with 500 ml of chloroform, the chloroform extracts combined and back extracted with 250 ml of a saturated solution of sodium bicarbonate and 250 ml of water. The chloroform layer is collected and dried over anhydrous magnesium sulfate. The solvent is removed by rotary evaporation in vacuo to yield 32 gm of a crude, tan-colored product. Recrystallization from 95% ethanol affords 25.3 gm (66% yield) of white crystals, M.P. 162°.

2. 5'-Azido-2',5'-dideoxyuridine

5'-O-Tosyl-2'-deoxyuridine (2.78 gm, 10 mmole) is dissolved in 50 ml of dimethylformamide (DMF) and 0.98 gm (20 mmole) of lithium azide added. The solution is heated at 100° C for 2 hours, then cooled and filtered. DMF is removed in vacuo at 40° and the yellow residue dissolved in 200 ml of 50% aqueous methanol. 20 gm of Dowex 50 ($H^+$) resin are added and the solution stirred at room temperature for 30 minutes. After filtration, the solvent is reduced to 20–30 ml by rotary evaporation. As the solution becomes more and more concentrated, a white precipitate forms. The precipitate is collected by filtration, dried in vacuo over KOH pellets and recrystallized from 2-propanol to yield 2.05 gm (80% yield) of a white powder.

3. 5'-Amino-2',5'-dideoxyuridine

5'-azido-2',5'-dideoxyuridine (258 mg, 1 mmole) is dissolved in 50 ml of ethanol and 50 mg of 10% palladium carbon catalyst added. The suspension is maintained at atmospheric pressure in a hydrogenation apparatus for 2.5 hours before filtering through Celite. The solvent is removed in vacuo, the residue dissolved in water and applied to a column of Dowex 50 ($H^+$) resin. After washing the column with 100 ml of water, the 5'-amino-2',5'-dideoxyuridine is eluted with 100 ml of 1M $NH_4OH$. The solution is evaporated to dryness and the residue crystallized from ethanol-ether to provide the desired product, (127 mg, 56%).

4. 5'-Amino-2',5'-dideoxy-5-iodouridine

5'-amino-2',5'-dideoxyuridine (113 mg, 0.5 mmole) is dissolved in 25 ml of 0.1M sodium acetate buffer at pH 5.0. Mercuric acetate (636 mg, 2.0 mmole) is added, and the solution heated at 55° C for 8 hours. After cooling, excess mercuric ions are removed by treatment with Chelex 100 resin (3 gm). The resin is removed by filtration and 20 ml of a 0.1M solution of $I_2$ in 95% ethanol added. The nucleoside-$I_2$ mixture is kept at room temperature for 2 hours, then extracted three times with 25 ml of chloroform. The aqueous solution is evaporated to dryness and the residue dissolved in ethanol. The product is crystallized from ethanol-ether-petroleum ether (1:1:1) to give 141 mg (80% yield) of product.

EXAMPLE II

Synthesis of 5'-amino-2',5'-dideoxy-5-bromouridine

To a solution of 5'-amino-2',5'-dideoxyuridine (0.113 g 0.5 mmole) in 100 ml of 0.05 M sodium acetate buffer, pH 6.0, is added 0.8 g (2.5 mmole) mercuric acetate. The solution is heated at 60° C for 5 hours and cooled on ice. Chelex 100 resin, 20 g, is added and the slurry stirred for 15 minutes at 0° C. The resin is removed by filtration and 0.177 g (1.0 mmole) of N-bromosuccinimide is added. The solution is stirred at room temperature for 30 minutes. The extent of bromination is followed spectrophotometrically at 300 nm, and the reaction terminated by the addition of aniline-ethanol when the absorbance increase plateaus. The reaction mixture is applied directly to a 2 × 15 cm column of Dowex 50 (H⁺) resin, the column washed with 200 ml of water, and eluted with 1 molar ammonium hydroxide. The solvent is removed at 40° C under reduced pressure, and the residue crystallized from ethanol-ether to provide 100 mg (69%) of the desired product.

EXAMPLE III

Acid Addition Salts

A total of 177 mg (0.5 mM) of 5'-amino-2',5'-dideoxy-5-iodouridine is suspended in distilled water and 0.55 ml of 1M HCl was added slowly with stirring to provide a solution of the amine hydrochloride salt. The salt is recovered by freeze-drying.

Other acid addition salts, specifically the salts of sulfuric, phosphoric, acetic, lactic, citric and tartaric are similarly prepared.

The salts of the corresponding bromo compound are also prepared by the same procedure.

The products of this invention may be administered alone, but will generally be administered with pharmaceutically acceptable, non-toxic carriers, the proportions of which are determined by the suitability and chemical nature of the particular carrier, the chosen route of administration, and standard pharmaceutical practice. For example, in combatting various infections or in maintaining therapeutically effective levels in the blood or tissues, they may be administered orally in the form of tablets or capsules containing such excipients as starch, milk sugar, certain types of clay, etc. They may be enteric coated so as to be more resistant to the acid and digestive enzymes of the stomach. For intravenous and intramuscular administration they may be used in the form of a sterile solution containing other solutes, for example, enough saline or glucose to make the solution isotonic. A wide variety of dosage unit forms are possible.

The physician or veterinarian in attendance will determine the dosage regimen which will be effective. This will depend upon such factors as the age and weight of the patient, the degree and locus of the infection and the dosage unit form selected. Dosage unit forms containing from 25 to 250 mg are useful.

The compounds of this invention manifest as inhibition of the order of 90% with the monkey cell line Vero infected with herpes simplex at a concentration as low as 40 $\mu$M. No cytotoxicity is evident, even at treatment levels as high as 200 $\mu$M. Comparable compounds which have been suggested as antiviral agents do not combine this high order of activity with low toxicity. For example, idoxuridine, while it shows a high order of activity at relatively low levels, is almost totally cytotoxic at a concentration of 50 $\mu$M.

Standard procedures were used to maintain the virus and the Vero cells. This included growth and titration by plaque assay as well as the replications of the virus in the presence of the test compounds. Cells were maintained and infected in Dulbecco's medium with 10% fetal calf serum.

For testing, the cells were infected with virus at a ratio of approximately 10 plaque forming units per cell. The viral inoculum was drained after one hour adsorption at 37° C. An appropriate volume of medium containing the compound for testing was added. After 36 – 48 hours at 37° C, the infected cells were frozen until ready for titration.

In similar studies, this lack of cytotoxicity was demonstrated in a variety of mammalian cells in culture, including those from humans, mice, hamsters and chickens.

The compounds of this invention 5'-amino-2',5'-dideoxy-5-iodouridine (AIU) and the corresponding bromo compound (ABrU) as well as the pharmaceutically acceptable salts of these compounds are particularly useful for the treatment of herpes simplex keratitis in mammals.

At the present time, the generally accepted therapy for acute herpes simplex keratitis includes the use of 5-iodo-deoxy-uridine (IdUrd). Although the clinical value of this compound has been well established, there is a need for alternative antiviral therapy for ocular herpetic infections. IdUrd-resistant strains of herpes simplex virus Type 1 have been found. Additionally, the compound exhibits significant cellular toxicity. This is manifested in undesirable side effects such as the development of follicular and papillary conjunctivitis, and epithelial punctate keratopathy.

For these and other reasons including teratogenicity of IdUrd which has been demonstrated in newborn rats following systemic administration and in pregnant rabbits receiving the drug topically to the eye in doses similar to those used clinically in humans, efforts have been made to find replacement therapeutics.

One advantage of AIU has been established by the treatment of rabbits. In this study, experimental herpes simplex keratitis was established bilaterally in 40 rabbits. These were divided into 5 matched groups of 8. Each group was treated in a double blind fashion with topical drops at 4 hour intervals for 72 hours starting 24 hours after infection. The solutions administered were:

1. Saline;
2. IdUrd, 1 mg/ml;
3. AIU, 1 mg/ml;
4. AIU, 4 mg/ml;
5. AIU, 8 mg/ml.

Each eye was examined daily for 14 days and graded by two ophthalmologists. IdUrd and AIU at 8 mg/ml were most effective therapeutically. Although IdUrd had the most immediate effect, cessation of the treatment was followed by the appearance of new ulcers. This effect was not observed with AIU. The AIU at 1 and 4 mg/ml were less potent than the more concentrated dosage units, but showed more rapid healing than the saline control.

In contrast to IdUrd, AIU manifests a much lesser teratological effect in suckling mice than does IdUrd. This was shown by a study in which 6 cages wih 10 mice (1–2 days old) with one mother in each were divided into 5 groups and injected once a day for the 5 following days as indicated below.

| I | PBS | Controls |
|---|-----|----------|
| II | AIU | 250 mg/kg |
| III | AIU | 450 mg/kg |
| IV | IdUrd | 125 mg/kg |
| V | IdUrd | 250 mg/kg |

The controls were treated with phosphate buffered saline solution. The Groups I-V comprised 2 mice in each cage. Because of the "mothering" effect, only 14 mice survived. These were sacrificed on the 25th day after onset of treatment.

The eyes were enucleated and fixed with 10% formalin. The mice which had been treated with IdUrd weighed 20 to 30% less than the controls, and inhibition of hair growth was evident. Visually observed, the mice looked sick. The AIU mice, on the other hand, appeared to be healthy and weighed nearly as much as the controls.

With the IdUrd mice, there were signs of immaturity in cornea, ciliary body and evident cataracts. There was marked reduction of the retinal width. The most striking changes were in the peripheral retina:

1. thinning out and ondulation of the outer nuclear layer;
2. disappearance of outer plexiform layer;
3. disorder in both nuclear layers, scattered nuclei of outer nuclear layer in region of inner nuclear layer, and
4. hypoplasia of rods and cones and, mostly peripherally, aplasia of rods and cones were noticed. These changes were marked in IdUrd dosage of 250 mg/kg and less evident in IdUrd 125 mg.

All of the above studies suggest significant advantages for the compounds of this invention compared with presently available therapeutic agents.

What is claimed is:

1. A compound selected from the group consisting of 5'-amino-2',5'-dideoxy-5-iodouridine; 5'-amino-2',5'-dideoxy-5-bromouridine; and the pharmaceutically acceptable acid addition salts thereof.
2. 5'-Amino-2',5'-dideoxy-5-iodouridine.
3. 5'-Amino-2',5'-dideoxy-5-bromouridine.
4. A pharmaceutical composition containing an effective amount of a compound for treating herpes simplex virus infection in mammals, said compound being selected from the group consisting of 5'-amino-2',5'-dideoxy-5-iodouridine; 5'-amino-2',5'-dideoxy-5-bromouridine and the pharmaceutically acceptable acid addition salts thereof together with a pharmaceutically acceptable carrier.
5. A composition of claim 4 containing 5'-amino-2',5'-dideoxy-5-iodouridine.
6. A composition of claim 4 containing 5'-amino-2',5'-dideoxy-5-bromouridine.
7. A method of treating a herpes simplex virus infection in a host mammal afflicted with such infection which comprises administering to the said host an amount of a compound which is effective for treating a herpes simplex virus infection, said compound being selected from the group consisting of 5'-amino-2',5'-dideoxy-5-iodouridine, 5'-amino-2',5'-dideoxy-5-bromouridine and the pharmaceutically acceptable acid salts thereof.

* * * * *